US011602701B2

(12) United States Patent
Matravers

(10) Patent No.: US 11,602,701 B2
(45) Date of Patent: Mar. 14, 2023

(54) METHOD FOR EXTRACTION AND ISOLATION OF CANNABIS TERPENE AND AROMATIC ISOLATES FROM CANNABIS SATIVA AND CANNABIS INDICA

(71) Applicant: Xerbal USA, LLC., Fullerton, CA (US)

(72) Inventor: Peter Matravers, Fullerton, CA (US)

(73) Assignee: XERBAL USA, LLC., Fullerton, CA (US)

( * ) Notice: Subject to any disclaimer, the term of this patent is extended or adjusted under 35 U.S.C. 154(b) by 199 days.

(21) Appl. No.: 17/100,701

(22) Filed: Nov. 20, 2020

(65) Prior Publication Data

US 2021/0146274 A1    May 20, 2021

Related U.S. Application Data

(60) Provisional application No. 62/938,200, filed on Nov. 20, 2019.

(51) Int. Cl.
*B01D 3/14*    (2006.01)
*B01D 3/38*    (2006.01)
(Continued)

(52) U.S. Cl.
CPC ........ *B01D 11/0203* (2013.01); *A61K 36/185* (2013.01); *B01D 3/14* (2013.01);
(Continued)

(58) Field of Classification Search
CPC ........ B01D 11/0203; B01D 3/14; B01D 3/38; B01D 11/0284; B01D 11/0288;
(Continued)

(56) References Cited

U.S. PATENT DOCUMENTS 9,649,349 B1 * 5/2017 Tucker ............... B01D 11/0288
9,744,200 B1 * 8/2017 Tucker .................. B01D 3/143
(Continued)

*Primary Examiner* — Joseph W Drodge
(74) *Attorney, Agent, or Firm* — Lapple Ubell IP Law, LLP.; Matthew C. Lapple

(57) ABSTRACT

A method for extracting and isolating terpenes and aromatic compounds from *Cannabis* plant material by the steps of grinding the *cannabis* plant material to obtain a ground *cannabis*, performing a CO2 supercritical extraction upon a first portion of the ground *cannabis*, wherein said supercritical extraction is performed at temperature below freezing, between −30 to 0 centigrade, for a period of 3 to 5 hours, at between 1000-1300 psi, performing a steam distillation upon a second portion of the ground *cannabis*, performing a butane extraction upon a third portion of the ground *cannabis*, wherein the butane extraction is performed at a temperature between −30 to 0 centigrade, performing an alcohol extraction upon a fourth portion of the ground *cannabis*, wherein the alcohol extraction is performed at a temperature between −30 to 0 centigrade, performing a maceration upon a fifth portion of the ground *cannabis*, wherein the maceration is performed with coconut oil at a temperature of between 40-70 centigrade, combining at least a portion of each of the resultant extracts from the CO2 supercritical extraction step, the steam distillation step, the butane extraction step, the alcohol extraction step and the maceration step to create a combined extract, and then fractionally distilling the combined extract to separate terpenes and other aromatic compounds from the combined extract.

6 Claims, 7 Drawing Sheets

(51) Int. Cl.
*B01D 11/02* (2006.01)
*A61K 36/18* (2006.01)
*A61K 36/185* (2006.01)

(52) U.S. Cl.
CPC ............ *B01D 3/38* (2013.01); *B01D 11/0284* (2013.01); *B01D 11/0288* (2013.01); *B01D 11/0292* (2013.01)

(58) Field of Classification Search
CPC .. B01D 11/0292; B01D 3/146; B01D 11/028; A61K 36/18; A61K 36/185; C11B 1/02; C11B 1/10; C11B 1/104; C11B 1/108; C11B 3/001; C11B 3/006; C11B 3/12; C11B 3/14; C11B 3/16; C07C 37/70; C07C 37/74; C07C 37/76
See application file for complete search history.

(56) References Cited

U.S. PATENT DOCUMENTS

| | | | |
|---|---|---|---|
| 9,950,275 B1* | 4/2018 | Ruben | C11B 3/006 |
| 2004/0147767 A1* | 7/2004 | Whittle | B01D 11/028 |
| | | | 549/390 |
| 2018/0344786 A1* | 12/2018 | Thacker, Jr. | A61K 31/045 |
| 2018/0344790 A1* | 12/2018 | Vu | A24D 1/18 |
| 2020/0054962 A1* | 2/2020 | Vanaman | B01D 3/38 |

\* cited by examiner

FIGURE 1A

Extraction Method:

1. CO2 process- Cold extraction with a specified volume of liquid carbon dioxide for 4 hours at minus 30 to 0C.

A packing density of 0.3 to 0.6 loosely packed. Supercritical conditions of 69 bar (1000 psi) for 4 hours, (1 psi=0.0689 bar)

The ideal moisture content for completely cured cannabis is between eight percent (8%) and ten percent (10%).

Curing is done to reduce the moisture content of the plant. This is especially important for CO2 extraction as this process has water content limitations.

Water content is one of the key aspects in determining the quality of the output of CO2 extraction processes.

The presence of water, however; may either assist in or be an impediment to the diffusion of supercritical carbon dioxide; what is necessary for effective extractions depends on the type of compounds targeted.

In our Cannabis extraction, we verified the effects of moisture content on the extraction of essential oils and they observed that pre-soaking of the samples in 1% 1 N Sodium Hydroxide (ie. 1% aqueous Sodium hydroxide solution) led to an increase in the extraction yield of 40% terpenes with the operating parameters described above.

2. Ethanol process- Cold extraction using four to one (4:1) ethanol to biomass ratio, steep and mix for 3 hours at minus 30 to 0C.

3. Butane process- Cold extraction using Butane extraction equipment. Must be able to keep 25 kilograms of butane at minus 30-40C, while maintaining ancillary chiller.

Starting material is Cannabis 7mm trim.

Extractor input of 4,500 grams Butane.

Return ratio of 0.15 (meaning the weight of extracts will be 15 percent of the weight of the plant material used)

FIGURE 1B

4. Steam process- comprises contacting the cannabis terpene material with a heated gas at a temperature of 105°C to 200°C, and for a time which is sufficient to volatilize one or more terpene to form a vapor but does not cause pyrolysis of the cannabis plant materials and condensing the vapor to form a terpene rich yield.

5. Maceration with coconut oil process- the Grind Dried 7mm Cannabis coarse powdery flakes is soaked and mixed in warm coconut oil (4:1 ratio) for 3 hours. Mixing is intermittent for 15 mins every one hour.

FIGURE 2
The extraction
1 kg Cannabis Biomass
Divided to 5x 200g portions for 5 separate extraction
1kg Cannabis trimmed biomass
200g 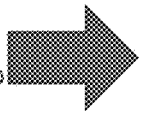 200g 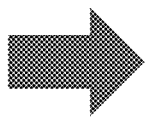 200g 200g 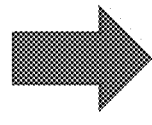 200g
Butane crude 150g, alcohol crude 150g (after ROH recovery), 150g distillation crude, Co2 crude 100g, 800g maceration crude
1,350g for fractional distillation
Yield 10 g terpene & isolates (1% of biomass)

FIGURE 3A

High Selectivity Factional Distillation Analysis on terpenes types: 7 samples

| Ingredient isolate over 0.5% in each fraction | Fraction B Ext temp 145-149°C | Fraction C Ext temp 175-179°C | Fraction D Ext temp 187-192°C | Fraction E Ext temp 194-198°C | Fraction F Ext temp 200-205°C | Fraction G Ext temp 208-212°C | Rectified Not distilled in container | Boiling point in C |
|---|---|---|---|---|---|---|---|---|
| 1 | 2 | 3 | 4 | 5 | 6 | 7 | | |
| Humulene 0.67 | Humulene <0.5 | Humulene <0.5 | Humulene <0.5 | Humulene 0.77 | Humulene 1.53 | Humulene 6.55 | | 106C |
| B Carophyllene 2.97 | B Carophyllene <0.5 | B Carophyllene 1.3 | B Carophyllene 1.92 | B Carophyllene 4.28 | B Carophyllene 8.72 | B Carophyllene 26.76 | | 130C |
| Alpha pinene 21.41 | Alpha pinene 19.55 | Alpha pinene 13.15 | Alpha pinene 7.89 | Alpha pinene 1.94 | Alpha pinene 0.58 | traces | | 155C |
| Camphene 2.12 | Camphene 2.12 | Camphene 1.68 | Camphene 1.19 | Camphene <0.5 | Camphene <0.5 | traces | | 159C |
| Sabinene 4.95 | Sabinene 4.70 | Sabinene 4.38 | Sabinene 4.11 | Sabinene 1.91 | Sabinene <0.5 | traces | | 163C |
| Beta pinene 13.47 | Beta pinene 15.92 | Beta pinene 15.09 | Beta pinene 13.48 | Beta pinene 7.16 | Beta pinene 2.84 | traces | | 165C |
| Myrcene 15.12 | Myrcene 16.91 | Myrcene 16.85 | Myrcene 15.06 | Myrcene 9.19 | Myrcene 3.37 | traces | | 167C |
| Delta 3 Carene 2.47 | Delta 3 Carene 3.04 | Delta 3 Carene 3.38 | Delta 3 Carene 3.49 | Delta 3 Carene 2.79 | Delta 3 Carene 1.33 | traces | | 170C |
| Beta Phellandrene | Beta Phellandrene | Beta Phellandrene | Beta Phellandrene | Beta Phellandrene | Beta Phellandrene | traces | | 171C |

FIGURE 3B

| | | | | | | | |
|---|---|---|---|---|---|---|---|
| 2.86 | 3.76 | 4.59 | 5.50 | 6.19 | 4.51 | traces | 172C |
| Alpha phellandrene 0.93 | Alpha phellandrene 1.14 | Alpha phellandrene 1.29 | Alpha phellandrene 1.34 | Alpha phellandrene 1.16 | Alpha phellandrene 0.6 | traces | 174C |
| Terpinolene isomer 2.32 | Terpinolene isomer 2.79 | Terpinolene isomer 3.90 | Terpinolene isomer 0.5 | Terpinolene isomer 8.59 | Terpinolene isomer 0.96 | traces | 176C |
| 1,8 Cineole 2.86 | 1,8 Cineole 3.76 | 1,8 Cineole 4.59 | 1,8 Cineole 5.50 | 1,8 Cineole 6.19 | 1,8 Cineole 4.51 | traces | 176C |
| Limonene 12.51 | Limonene 15.72 | Limonene 19.33 | Limonene 22.63 | Limonene 25.15 | Limonene 17.26 | traces | 176C |
| B-Ocimene 0.83 | B-Ocimene 0.99 | B-Ocimene 1.28 | B-Ocimene 1.47 | B-Ocimene 1.86 | B-Ocimene 1.36 | traces | 193C |
| Fenchone 0.51 | Fenchone 0.58 | Fenchone 0.78 | Fenchone 1.05 | Fenchone 1.75 | Fenchone 2.62 | Linalool 3.07 | 198C |
| Linalool 2.99 | Linalool 3.26 | Linalool 4.62 | Linalool 6.40 | Linalool 1.48 | Linalool 18.78 | Alpha Terpineol 2.69 | 219C |
| α – Terpineol | α – Terpineol | α – Terpineol | α – Terpineol | Alpha Terpineol 1.82 | Alpha Terpineol 3.70 | Borneol 1.28 | 213C |
| Borneol | Borneol | Borneol | Borneol | Borneol 1.26 | Borneol 2.48 | | 213C |
| isoborneol | isoborneol | isoborneol | isoborneol | isoBorneol 0.82 | isoBorneol 0.82 | | 229C |
| Neral | | | | | Neral 0.77 | Geranial 1.51 | 229C |
| Geranial | Geranial | Geranial | Geranial | Geranial 0.55 | Geranial 0.99 | | |

FIGURE 3C

| | | | | | | |
|---|---|---|---|---|---|---|
| Geraniol | Geraniol | Geraniol | Geraniol 0.53 | Geraniol 1.07 | Geraniol 1.55 | 230C |
| Eugenol | Eugenol | Eugenol | Eugenol | Eugenol 0.54 | Eugenol 2.09 | 254C |
| Nerolidol 2.41 | Nerolidol <0.5 | Nerolidol <0.5 | Nerolidol 1.26 | Nerolidol 2.19 | Nerolidol 28.42 | 276C |
| Caryophylline oxide | Caryophylline oxide | Caryophylline oxide | Caryophylline oxide | Caryophylline oxide | Caryophylline oxide 2.30 | 279C |
| Plus over 100 other isolates, each <0.5% | Plus over 100 other isolates, each <0.5% | Plus over 100 other isolates, each <0.5% | Plus over 100 other isolates, each <0.5% | Plus over 100 other isolates, each <0.5% | Plus over 100 other isolates, each <0.5% | |
| 98% | 98% | 98% | 98% | 98% | 98% | |

Note: Fraction A was discarded

FIGURE 4

| Item Tested | | Aliphatic and Terpanic Alcohols | | Monoterpenes | | Sesquiterpenes | | All Others | |
|---|---|---|---|---|---|---|---|---|---|
| %Analyzed | | % | %Norm | % | %Norm | % | %Norm | % | %Norm |
| 98.13 | PM Blend B | 12.71 | 12.95 | 51.95 | 52.94 | 16.24 | 16.55 | 17.23 | 17.56 |
| 98.36 | Fraction B | 10.35 | 10.52 | 81.67 | 83.03 | 4.16 | 4.23 | 2.18 | 2.22 |
| 98.23 | Fraction C | 6.74 | 6.86 | 89.07 | 90.67 | 1.45 | 1.48 | 0.97 | 0.99 |
| 98.56 | Fraction D | 8.07 | 8.19 | 87.61 | 88.89 | 1.74 | 1.77 | 1.14 | 1.16 |
| 99.03 | Fraction E | 10.98 | 11.09 | 83.92 | 84.74 | 2.61 | 2.64 | 1.52 | 1.53 |
| 98.44 | Fraction F | 20.16 | 20.48 | 69.68 | 70.78 | 5.7 | 5.79 | 2.9 | 2.95 |
| 97.73 | Fraction G | 16.07 | 16.44 | 45.76 | 46.82 | 12.13 | 12.41 | 23.77 | 24.32 |
| 95.22 | Rectified Fraction | 41.01 | 43.07 | 1.25 | 1.31 | 37.91 | 39.81 | 15.05 | 15.81 |

METHOD FOR EXTRACTION AND ISOLATION OF CANNABIS TERPENE AND AROMATIC ISOLATES FROM CANNABIS SATIVA AND CANNABIS INDICA

FIELD OF THE DISCLOSURE

The embodiments of the described invention relate generally to a method of extraction and isolation of cannabinoids, terpenes and other aromatic isolates from plant material, particularly from *Cannabis sativa* and *Cannabis indica*.

BACKGROUND

*Cannabis*, also commonly known as marijuana, is a flowering plant that includes three species (or sub-species), namely *sativa*, *indica* and *ruderalis*. A closely related agricultural plant, which is sometimes also called "*cannabis*", is what is otherwise known as "hemp" or "industrial hemp." The *cannabis* plant is indigenous to Central Asia and the Indian Subcontinent. *Cannabis* has long been used for hemp fiber, for oils, for medicinal purposes and as a recreational drug. *Cannabis* plants produce a group of chemicals called cannabinoids. The majority of these compounds are secreted by glandular trichomes that occur abundantly on the floral calyxes and bracts of female *cannabis* plants. When used by humans medicinally or recreationally, *cannabis* can be consumed by a variety of routes, including vaporizing or smoking dried flower buds and leaf portions, resins, extracted oils or waxes.

The most well-known cannabinoid is tetrahydrocannabinol, often abbreviated as "THC." The chemical formula for THC is $C_{21}H_{30}O_2$ and it has the following chemical structure:

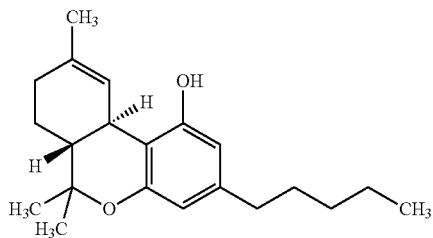 [SMILES: CCCCCc1cc(O)c2c(c1)OC(C)(C)[C@@H]1CCC(C)=C[C@@H]21]

THC is widely recognized as the principal psychoactive constituent in *cannabis*. THC has a very low solubility in water, but good solubility in most organic solvents, specifically lipids and alcohols.

The *cannabis* plant produces hundreds of other cannabinoids, terpenoids and other compounds that are only beginning to be identified, studied and categorized. One generally recognized cannabinoid that has medical efficacy is Cannabidiol ("CBD"). It is a major constituent of the plant, second to THC, and represents up to 40% by weight, in its extracts. Compared with THC, CBD is not psychoactive in healthy individuals, and is considered to have a wider scope of medical applications than THC, including for epilepsy, multiple sclerosis spasms, anxiety disorders, bipolar disorder, schizophrenia, nausea, convulsion and inflammation, as well as inhibiting cancer cell growth.

Another known cannabinoid is Cannabinol ("CBN"). CBN is a non-psychoactive cannabinoid found only in trace amounts in growing or recently harvested *Cannabis*, but is mostly found in aged *Cannabis*. Pharmacologically relevant quantities of CBN are formed as a metabolite of tetrahydrocannabinol THC. CBN acts as a partial agonist at the CB1 receptors, but has a higher affinity to CB2 receptors; however, it has lower affinities relative to THC. Anecdotally, CBN is believed to be sleep-inducing.

Unlike other cannabinoids, CBN does not stem directly from cannabigerol ("CBG") or cannabigerolic acid ("CBGA"), but rather is the degraded product of tetrahydrocannabinolic acid ("THCA"). If harvested *cannabis* is exposed to oxygen and/or ultraviolet light (for example, in sunlight) for a prolonged period of time, THCA will convert to cannabinolic acid ("CBNA"). CBN is then formed by decarboxylation of CBNA.

As investigation and research regarding *cannabis* and its effects upon human physiology have progressed, greater knowledge and understanding has developed regarding the presence and effects of various non-cannabinoid, aromatic compounds found in *cannabis*, which are known generally as "terpenes." Many different terpenes may be present in different strains of *cannabis*, in different concentrations. Indeed, over two-hundred different terpenes have been identified as present in one or more strains of *cannabis*. In some cases, the presence of different terpenes, in different amounts, will have a meaningful impact on the physical and psychoactive effects that a *cannabis* consumer will experience. Many believe that certain terpenes have medical benefits. Further, terpenes are believed to be an integral component of the "entourage effect." The "entourage effect" is thought by researchers to be a multifaceted combination of cannabinoids and terpenoids occurring in various measure in a *cannabis* infused smokable or edible product. The significance of the "entourage effect" is that it is believed that cannabinoids, for example, THC and/or CBD interact more effectively with the CB1 and CB2 receptors in the brain, as well as greater efficacy regarding cannabinoid interaction with the endocannabinoid system in the central nervous system. The absence of this multiplicity of cannabinoids and terpenoids or "entourage effect," as demonstrated by isolated THC or CBD, can result in suboptimal health benefits in human beings, relatively speaking. Moreover, terpenes are known to be present in many different non-*cannabis* plants and are responsible for many common aromas and tastes. Terpenes are the main aromatic compounds in many plant-derived essential oils. Terpenoids are pharmacologically versatile: they are lipophilic, interact with cell membranes, neuronal and muscle ion channels, neurotransmitter receptors, G-protein coupled (odorant) receptors, second messenger systems and enzymes (Bowles, 2003; Buchbauer, 2010). All the terpenoids discussed herein are "Generally Recognized as Safe," as attested by the US Food and Drug Administration as food additives, or by the Food and Extract Manufacturers Association and other world regulatory bodies. Terpenoid components in concentrations above 0.05% are considered of pharmacological interest (Adams and Taylor, 2010). Mice exposed to terpenoid odors inhaled from ambient air for 1 hour demonstrated profound effects on activity levels, suggesting a direct pharmacological effect on the brain, even at extremely low serum concentrations (examples: linalool with 73% reduction in motility at 4.22 ng·mL-1, pinene 13.77% increase at trace concentration, terpineol 45% reduction at 4.7 ng·mL-1). These levels are comparable to those of THC measured in humans receiving *cannabis* extracts yielding therapeutic effects in pain, or symptoms of multiple sclerosis in various randomized controlled trials (RCTs) (Russo, 2006; Huestis, 2007). Positive effects at undetectable serum concentrations with orange terpenes (primarily limonene, 35.25% increase in mouse activity), could be explainable on the basis of rapid redistribution and concentration in lipophilic cerebral structures. A similar rationale pertains to human studies (Komori et al., 1995), subsequently discussed. Limonene is highly bioavailable with 70% human pulmonary uptake (Falk-Filipsson et al., 1993), and a figure of 60% for pinene with rapid metabolism or redistribution (Falk et al., 1990). Ingestion and percutaneous absorption is also well documented in humans, 1500 mg of lavender EO with 24.7% linalool (total 372 mg) was massaged into the skin of a 60 kg man for 10 min, resulting in a peak plasma concentration of 100 ng·mL-1 at 19 min, and a half-life of 13.76 min in serum (Jager et al., 1992). Various terpenes that have been identified as sometimes being present in *cannabis* include, but are not limited to:

Myrcene, including Beta-Myrcene: The odor of Myrcene is variously described as clove-like, earthy, nutty, green-vegetative and citrus-like. Myrcene is also present in large concentrations in hops, lemon grass, the West Indian Bay tree, *verbena*, and mangos, and particularly in slightly overripe mangos. Myrcene is believed to be a potent analgesic, anti-inflammatory and antibiotic. Myrcene is also believed to be a synergist to THC, and may create a stronger psychoactive effect/experience than THC alone. Myrcene also may affect the permeability of cell membranes and either enable THC to cross the blood-brain barrier more effectively, or serve as a carrier of the THC molecule in this action. Myrcene is also believed to be responsible for the sleepy or relaxed feeling associated with the consumption of some strains of *cannabis*, and is believed by some to contribute to the "couch-lock" effect of some strains of *cannabis*. Herbal medicines containing myrcene have a long history of being used as a sleep aid in folk medicine. In Mexico, myrcene-rich lemongrass infused tea has been used in as a sedative and muscle relaxant. It is common for Germans, who are the second largest hops growers in the world (the US is first), to use myrcene-rich hops preparations as a sleep aid.

Limonene: Limonene is found in the rind of citrus fruits, such as lime and lemon, as well as many other fruits and flowers. The odor of Limonene is commonly described as citrus, lime or lemony. Limonene is believed to have anti-bacterial, anti-fungal and anti-cancer activities. It is believed to inhibit the Ras cancer gene cascade which promotes tumor growth. In humans, Limonene quickly permeates the blood-brain barrier and promotes the absorption of other terpenes, as well as an increase in systolic blood pressure. Limonene is variously associated with and believed to be responsible for *cannabis* consumer's feelings of alertness, restlessness, increased sexuality, buoyancy and focused attention. Limonene has a wide range of benefits, including its ability to help with focus and lift your mood. Limonene can also quell stress and help fight depression and anxiety. In addition to its positive mental health perks, limonene has anti-fungal, anti-bacterial, and even anti-cancer properties. As for specific strains containing limonene, it's found more frequently (but not exclusively) in *sativa* strains, while certain hybrid and *indica* varieties can also contain high levels of this particular terpene as well.

Caryophyllene, including Beta-Caryophyllene ("B-Caryophyllene") and Trans-Caryophyllene: Caryophyllene is described as having a sweet, woody, dry-clove odor. Caryophyllene's taste is described as peppery spicy with camphor and astringent citrus backgrounds. Caryophyllene is found in black pepper, cloves, and cotton, as well as in other herbs and spices. When ingested in large amounts, B-Caryophyllene may block calcium and potassium ion channels. As a result, it may impede pressure exerted by heart muscles. Applied topically, B-Caryophyllene is an analgesic and one of the active constituents of clove oil, a natural and preferred treatment for toothache. It may also help reduce inflammation. Among *cannabis* consumers, B-Caryophyllene is believed to be responsible for good or positive feelings and slight giddiness. Caryophyllene is a common and often abundant terpene found in *cannabis*. Its distinctive flavor contributes to the spiciness of black pepper and can be found in high amounts in cloves, hops, and rosemary. It falls under the FDA's "generally recognized as safe" classification. CB2 receptors are found in immune tissues throughout the body and are increased in the brain in disease or following injury. Beta caryophyllene activates these receptors, reduces inflammation, which lessens pain and reduces the damaging consequences that chronic inflammation has on brain function and risk for developing brain diseases.

Caryophyllene oxide has the capability of binding with the human body's endocrine CB2 receptors. It is believed to be the only terpene in *cannabis* that can successfully bind with CB2. This unique skill is believed to make it highly beneficial for medicinal uses such as an anti-inflammatory, local anesthetic, antioxidant, and perhaps in cancer treatment.

Pinene, including Alpha-Pinene and Beta-Pinene: Pinene is the familiar odor associated with pine trees and their resins. Pinene is the major component in turpentine (note that the archaic spelling of "terpentine" gives the entire class of aromatic terpenes its name). Pinene is also commonly found in rosemary, sage and *eucalyptus*. Pinene is sometimes used as an expectorant and a topical antiseptic. It easily crosses the blood-brain barrier and is believed to act as an acetylcholinesterase inhibitor, resulting in improved memory. Pinene is also believed to be a bronchodilator. Pinene is likely to strongly contribute to, or create, the "skunk" odor that is often associated with *cannabis*. Among *cannabis* consumers, Pinene is believed to increase focus, self-satisfaction, and energy. Many studies have shown that alpha-pinenes offer solid health benefits including: Anti-cancer properties; Anti-inflammatory benefits; Bronchodilator—especially when working in synergy with THC; Broad spectrum antibiotic properties—highly effective against MRSA when working in synergy with the cannabinoids CBD and CBN; Increases alertness and counteracts some of the ill-effects of THC such as anxiety; Works to improve benefits with the entourage effect on cannabinoids like THC; Can decrease oil production in overly oily skin Terpineol: Terpineol has a lilac, citrus, lime or apple blossom odor and is also often perceived as slightly sweet smelling. It is a minor constituent in many plant essential oils and is sometimes used in perfumes and soaps. Terpineol is believed to result in reduced motility, or capability for movement, and has done so in certain rat studies. Among *cannabis* consumers, Terpineol may account for the reduced motility effect ("couch-lock") associated with some strains of *cannabis*. The odors of Terpineol in *cannabis* are often masked by the stronger odors of Pinene, which is often present in the same strains.

Borneol: Borneol has a menthol or camphor-like aroma. It is found in many plants, but is most commonly derived from *Artemisia* (also commonly known as "Wormwood") and some species of Cinnamon. Borneol is a calming sedative in Chinese medicine. Borneol may be responsible for both a calming effect and a psychedelic effect among *cannabis* consumers.

Delta-3-Carene: Delta-3-Carene has a sweet, pungent odor. It is found in many plants, including in pine and cedar resins and rosemary. Delta-3-Carene may cause drying or cessation of certain body fluids, such as tears and mucus. Delta-3-Carene may contribute to the dry eye and dry mouth effects experienced by some *cannabis* consumers.

Linalool: Linalool has a floral odor reminiscent of spring flowers such as Lilly-of-the-Valley, but with spice overtones. It is found in lavender and a number of other plants. Linalool is being tested as a cancer treatment. Linalool is believed to have a sedative effect. Linalool's anti-microbial properties are protective for the plant and represent a potential therapeutic use in people. Whether it was used as an early antibiotic is unknown, but linalool (often in the form of lavender or peanut stems and leaves) has been used in traditional medicine practices for its sedative and anti-epileptic properties. Linalool is also shown to reduce levels of anxiety and lower depression-like behaviors. Linalool also makes the immune system more resilient to the destructive effects of stress. Stress causes a shift in the distribution of white blood cells in the body (i.e., the cells of the immune system); the percent of lymphocytes decrease, and neutrophils increase.

Pulegone: Pulegone has a minty-camphor odor and flavor and is used in the candy industry. In very high dosages it is implicated in liver damage. Pulegone is found in very small concentrations in *cannabis*, but is believed to be an acetylcholinesterase inhibitor, and may partially counteract THC's effect of lowering acetylcholine levels.

Cineole, including 1.8-Cineole or Eucalyptol: Cineole has a camphor-minty odor and is the main component in oil of *eucalyptus*. Cineole is believed to increase circulation and provide topical pain relief. Cineole, like *eucalyptus* oil, may contribute to the feelings of centering, balancing, stimulating and thought-provoking experienced by some *cannabis* consumers.

Ocimene: Ocimene is recognized by its sweet, fragrant, herbaceous, and woodsy aromas. Ocimene is also found in botanicals as diverse as mint, parsley, pepper, basil, mangoes, orchids, cumquats and *cannabis*. Ocimene is believed to act as an antiviral, an antifungal, an antiseptic, a decongestant and an antibacterial.

Terpinoline: Terpinoline is characterized by a fresh, piney, floral, herbal and occasionally citrusy aroma and flavor. Terpinoline is also found in nutmeg, tea tree, certain confers, apples, cumin and lilacs. Terpinoline is believed to act as an anticancer agent, an antioxidant, a sedative, an antibacterial and an antifungal. Terpinolene offers a mildly sedative effect and can reduce anxiety It also has antiseptic properties and it can help repel pests like mosquitoes and weevils.

Guaiol: Guaiol is not an oil, but a sesquiterpenoid alcohol, and is also found in cypress pine and guaiacum. Guaiol has been used in traditional medicine as a treatment for diverse ailments ranging from coughs to constipation to arthritis. It is also used as an insect repellent and insecticide. It is believed that Guaiol has antimicrobial and anti-inflammatory properties.

Bisabolol, including A-Bisabolol or Levomenol: Bisabolol is a fragrant terpene that is also found in the chamomile flower and the candeia tree. Bisabolol is believed to be an anti-inflammatory, an anti-irritant, an antioxidant, an anti-microbial, and an analgesic.

Nerolidol: Nerolidol is a terpene that gives certain *cannabis* strains a distinctive woody aroma. Besides contributing the scent profile, nerolidol can also be used as an antifungal agent or as a natural sleep aid. A study published in 2007 examined nerolidol's effects on skin lesions in guinea pigs and found that it was clinically effective at treating lesions within the first week of application.

Humulene: Humulene has a subtle earthy, woody aroma with spicy herbal notes. It is also found in cloves, basil, and hops. It is believed to suppress hunger and is also believed to be an anti-bacterial, an anti-inflammatory, an anti-tumor agent, and a pharmacokinetic.

Geraniol: Geraniol provides the distinctive and delicate aroma of geranium flowers and is sometimes described as smelling like citronella, roses, passionfruit or stonefruit such as peaches or plums. Geraniol is also found in a wide range of plants including tobacco, lemons. Interestingly it is also produced and used by honey bees as a chemical marker or signal. Geraniol is believed to be an antioxidant, an anti-tumor agent, a neuroprotectant, an anti-bacterial, an antifungal and an antispasmodic.

Neral/Geranial—Because of their delightful citrus scent, both geranial and neral are often used in perfumes and personal care products. They have anti-allergic and anti-inflammatory effects. They are also good for relieving digestive upsets such as cramps and spasms and can help reduce muscle pain.

Valencene: Valencene has citrusy sweet aromas and flavors of oranges, grapefruits, tangerines and occasionally of fresh herbs or freshly cut wood. Valencene derives its name from the fact that it is commonly found in Valencia oranges. It is a known repellent of ticks and mosquitos. Valencene is believed to be an anti-inflammatory and an insecticide Thujone: Thujone has a menthol odor. Thujone is found in a number of plants, such as arborvitae (genus *Thuja*, hence the derivation of the name), Nootka cypress, some junipers, mugwort, oregano, common sage, tansy, and wormwood, most notably grand wormwood (*Artemisia absinthium*), usually as a mix of isomers in a 1:2 ratio. It is also found in various species of Mentha (mint). Though it is best known as a chemical compound in the spirit absinthe, which contains only small quantities of Thujone, it is unlikely to be responsible for absinthe's alleged psychedelic effects. Thujone acts on GABA as an antagonist (opposite to the effects of alcohol) and as a component of several essential oils, is also used in perfumery. As a competitive antagonist of GABA, Thujone alone is considered to be convulsant, though by interfering with the inhibitory transmitter GABA, it may convey stimulating, mood elevating effects at low doses.

Moreover, terpenes can be used to derive related alcohols, aldehydes or ketones, referred to as "terpenoids" or "isoprenoids," by the addition of further functional groups, most commonly containing Oxygen. As used herein, the term "terpene" or "terpenes" refers to any known terpene, including but not limited to terpenoids or isoprenoids derived therefrom.

Terpenoids can provide adjunctive support. In a clinical trial, 48 cigarette smokers inhaled vapor from an EO of black pepper (Piper nigrum), a mint-menthol mixture or placebo (Rose and Behm, 1994). Black pepper EO reduced nicotine craving significantly (P<0.01), an effect attributed to irritation of the bronchial tree, simulating the act of cigarette smoking, but without nicotine or actual burning of material, suggesting a pharmacological effect. The terpenoid profile of black pepper suggests possible candidates: myrcene via sedation, pinene via increased alertness, or especially caryophyllene via $CB_2$ agonism and a newly discovered putative mechanism of action in addiction treatment. Results obtained in human depression solely with a citrus scent (Komori et al., 1995), strongly suggest the possibility of synergistic benefit of a phytocannabinoid-terpenoid preparation. Enriched odor exposure in adult mice induced olfactory system neurogenesis (Rochefort et al., 2002), an intriguing result that could hypothetically support plasticity mechanisms in depression (Delgado and Moreno, 1999), and similar hypotheses with respect to the ECS in addiction treatment (Gerdeman and Lovinger, 2003). Phytocannabinoid-terpenoid synergy might theoretically apply. Compelling confirmatory evidence in humans was provided in a clinical study (Komori et al., 1995), in which hospitalized depressed patients were exposed to citrus fragrance in ambient air, with subsequent normalization of Hamilton Depression Scores, successful discontinuation of antidepressant medication in 9/12 patients and serum evidence of immune stimulation (CD4/8 ratio normalization).

It is generally known that the concentrations of different terpenes are highly variable among different strains of cannabis. It is believed that these differences contribute, in part, to the variations in aroma, taste, physical, and psychoactive effects among different strains of cannabis.

It is also generally known that the concentrations of different terpenes, even in the same strain, can be highly variable based on cultivation practices, harvesting times, and post-harvest treatment of cannabis plants. For example, it is believed that the presence of and concentration of terpenes in cannabis can be influenced or manipulated by watering regimes, light exposure, light intensity, growing time, nutrient and mineral delivery regimes and amounts, harvest timing (e.g. how long a plant is allowed to grow before harvest), the amount of time taken to harvest (e.g., labor or equipment limitations may cause large growing operations to take long as 2-4 weeks between when the first plants are harvested and the last plants are harvested), and post-harvest treatment, (e.g., drying and curing vs. flash freezing of green materials).

It is also generally known that the processes of cannabis oil extraction and post-extraction processing of cannabis oil or resin frequently result in the evaporation or destruction of some amount of the terpenes present in the harvested cannabis plant material. Most terpenes have a relatively low boiling point and evaporate easily. Extraction processes that use hydrocarbon-based solvents normally require heating or distillation to remove those solvents, resulting in evaporation of at least some, and often most, terpenes present in the harvested plant material. Extraction processes that use supercritical CO2 are often better suited to preserve terpenes, but can also result in terpene removal or destruction.

It is also believed by many researchers that many of the other cannabinoids, terpenoids and other compounds may have important health benefits and/or be capable of treating certain human diseases.

In the early twentieth century, it became illegal in most of the world to cultivate or possess cannabis. However, within the last decade, some states and nations have begun to legalize the cultivation, possession and use of cannabis for medical purposes. Currently, the use of medical marijuana is decriminalized or legalized in many U.S. states. Cannabis is used to reduce nausea and vomiting during chemotherapy, to improve appetite in people with HIV/AIDS, to treat chronic pain, and help with muscle spasms. Other possible medical uses, which are sometimes disputed, include treatment of multiple sclerosis, AIDS wasting syndrome, epilepsy, rheumatoid arthritis, glaucoma, PTSD, depression and generalized anxiety.

Further, within the last five years, several states in the United States have legalized or decriminalized the cultivation, possession and use of Cannabis for recreational purposes. It is therefore estimated by many experts that cannabis consumption, for both medical and recreational purposes, will increase over the coming years.

Accordingly, there is a need for an improved method of extraction and isolation of cannabis terpenes and aromatic isolates from cannabis plant material, that addresses the issues and disadvantages of prior art approaches discussed above.

SUMMARY

Embodiments of the present invention address the needs described above and relate to an improved method of extraction and isolation of cannabis terpenes and aromatic isolates from cannabis plant material.

BRIEF DESCRIPTION OF THE DRAWINGS

In the descriptions that follow, like parts or steps are marked throughout the specification and drawings with the same numerals, respectively. The drawing figures are not necessarily drawn to scale and certain figures may be shown in exaggerated or generalized form in the interest of clarity and conciseness. The disclosure itself, however, as well as a preferred mode of use, further objectives and advantages thereof, will be best understood by reference to the following detailed description of illustrative embodiments when read in conjunction with the accompanying drawings, wherein:

FIGS. 1A-B illustrates a multi-step cannabis terpene extraction method as described herein;

FIG. 2 further illustrates the multi-step terpene extraction method via an exemplary extraction;

FIGS. 3A-C illustrates a high selectivity factional distillation analysis on terpenes types using seven samples; and FIG. 4 illustrates results from a fractional distillation.

DETAILED DESCRIPTION OF THE EMBODIMENTS

The description that follows is presented to enable one skilled in the art to make and use the present invention, and is provided in the context of a particular application and its requirements. Various modifications to the disclosed embodiments will be apparent to those skilled in the art, and the general principles discussed may be applied to other embodiments and applications without departing from the scope and spirit of the invention. Therefore, the invention is not intended to be limited to the embodiments disclosed, but the invention is to be given the largest possible scope which is consistent with the principles and features described herein.

Embodiments disclosed herein relate to a method of extracting terpenes and aromatic compounds from *cannabis* plant material, using multiple extraction/fractional distillation techniques, and recombining extracted compounds to achieve a broad spectrum mixture, that more closely reflects the balance of compounds found in natural *cannabis* plant material, than is otherwise achievable from conventional extraction methods.

The extraction methods include steam distillation, $CO_2$ extraction, Butane extraction, Ethanol extraction, and maceration in warm coconut oil. In certain embodiments, the five different processes yield different compounds, which can be followed by a final fractional distillation for high purity of *Cannabis* terpenes and aromatic isolates. In certain embodiments, the compounds can be kept separate, or can be recombined, as desired.

In one of its aspects the embodiments described herein relate to a method in which five different extracts, when combined yield a more complex *Cannabis* flavor profile unlike any conventional commercial *cannabis* terpenes available in the Market today.

In another of its aspects the embodiments described herein relate to a method in which extract is substantially completely removed from solvent by pressure variation where $CO_2$, Ethanol, Butane can be recovered and recycled.

In a further aspect of the invention it relates to a method in which said five combinations is further purified by Fractional distillation yielding six flavorful keys of different *cannabis* terpene/aromatic flavoring compounds.

Key elements to success in recovering more *Cannabis* flavoring compounds is due to the low temperature minus 30 C to 0 C for the solvents (ethanol, $CO_2$, Butane), Steam at 100 C, and maceration with coconut oil at 40 C. This temperature assortment enables a broader spectrum of compound variations and yield efficiency.

Biomass/*Cannabis* Plant Material Preparation:

The ideal moisture content for completely cured *cannabis* is between eight percent (8%) and 10%.

Curing is done to reduce the moisture content of the plant. Can accomplish this by a) placing biomass in a low-temperature oven until they were crispy. b) hang the biomass on racks in a barn for a few days.

Once the degree of dryness is verified around 8%, apply 1% w/w of 1N sodium Hydroxide solution. This can be accomplished by just spraying the biomass with the said solution.

This alkaline hydrolysis process help soften the lignin & cellulose fibers thus increase solvent penetration during the extraction process for higher yield. Amount of sodium hydroxide used (1% of 1 N w/w of biomass) does not react with the chemical content of the terpenes.

Then, grind the dried *cannabis* and/or the dried and alkaline hydrolysis treated *cannabis*, into coarse, powdery flakes of approximately 3-7 mm diameter.

Extractions

With reference to FIG. 1, steps involved in embodiments of method are disclosed and discussed. These steps include multiple different extractions, which can be performed either simultaneously, or in series, using *cannabis* plant material:

1. $CO_2$ process—Cold extraction with a specified volume of liquid carbon dioxide for 4 hours at minus 30 to 0 C.

A packing density of 0.3 to 0.6 loosely packed. Supercritical conditions of 69 bar (1000 psi) for 4 hours, (1 psi=0.0689 bar)

The ideal moisture content for completely cured *cannabis* is between eight percent (8%) and ten percent (10%).

Curing is done to reduce the moisture content of the plant. This is especially important for $CO_2$ extraction as this process has water content limitations.

Water content is one of the key aspects in determining the quality of the output of $CO_2$ extraction processes.

The presence of water, however; may either assist in or be an impediment to the diffusion of supercritical carbon dioxide; what is necessary for effective extractions depends on the type of compounds targeted.

In our *Cannabis* extraction, we verified the effects of moisture content on the extraction of essential oils and they observed that pre-soaking of the samples in 1% 1 N Sodium Hydroxide (ie. 1% aqueous Sodium hydroxide solution) led to an increase in the extraction yield of 40% terpenes with the operating parameters described above.

2. Ethanol process—Cold extraction using four to one (4:1) ethanol to biomass ratio, steep and mix for 3 hours at minus 30 to 0 C.

3. Butane process—Cold extraction using Butane extraction equipment. Must be able to keep 25 kilograms of butane at minus 30-40 C, while maintaining ancillary chiller, Starting material is *Cannabis* 7 mm trim.

Extractor input of 4,500 grams Butane.

Return ratio of 0.15 (meaning the weight of extracts will be 15 percent of the weight of the plant material used)

4. Steam process—comprises contacting the *cannabis* terpene material with a heated gas at a temperature of 105° C. to 200° C., and for a time which is sufficient to volatilize one or more terpene to form a vapor but does not cause pyrolysis of the *cannabis* plant materials and condensing the vapor to form a terpene rich yield.

5. Maceration with coconut oil process—the Grind Dried 7 mm *Cannabis* coarse powdery flakes is soaked and mixed in warm coconut oil (4:1 ratio) for 3 hours. Mixing is intermittent for 15 mins every one hour.

The extraction method is further illustrated and explained by FIG. 2, with exemplary amounts of *cannabis* plant material discussed, and the resultant yield disclosed.

With reference to FIG. 3, a high selectivity fractional distillation analysis of terpenes and aromatic compounds achieved on seven samples, using the disclosed method of FIGS. 1 & 2, is provided.

In one exemplary extraction, Applicant has been able to use the described method to achieve an extraction, and been able to isolate the following one-hundred-twenty-nine (129) terpenes & isolates, from *cannabis* plant material:

Tricyclene 0.11 Monoterpene
α-Thujene 0.03 Monoterpene
α-Pinene 7.77 Monoterpene
Camphene 0.90 Monoterpene
α-Fenchene 0.11 Monoterpene
Unknown 0.02 Monoterpene
Unknown 0.01 Unknown
meta-Cymene 0.02 Monoterpene
Sabinene 2.64 Monoterpene
β-Pinene 7.12 Monoterpene
Unknown 0.29 Monoterpene
cis-Carane 0.06 Monoterpene Octen-3-ol 0.02 Aliphatic alcohol
Dehydro-1,8-cineole 0.06 Monoterpenic ether
Myrcene 10.99 Monoterpene
trans-Carane? 0.17 Monoterpene
α-Phellandrene 0.67 Monoterpene
Pseudolimonene 0.01 Monoterpene
Δ3-Carene 1.73 Monoterpene
1,4-Cineole 0.01 Monoterpenic ether
α-Terpinene 0.04 Monoterpene
para-Cymene 0.14 Monoterpene
Limonene 11.25 Monoterpene
1,8-Cineole 2.57*Monoterpenic ether
β-Phellandrene [2.57]*Monoterpene
(Z)-β-Ocimene 0.45 Monoterpene
(E)-β-Ocimene 0.95 Monoterpene
γ-Terpinene 0.08 Monoterpene
cis-Sabinene hydrate 0.01 Monoterpenic alcohol
para-Mentha-3,8-diene 0.01 Monoterpene
cis-Linalool oxide (fur.) 0.03 Monoterpenic alcohol
Octanol 0.01 Aliphatic alcohol
Fenchone 0.75 Aliphatic alcohol
Terpinolene isomer 0.36 Monoterpene
Terpinolene 3.34 Monoterpene
para-Cymenene 0.10 Monoterpene
6,7-Epoxymyrcene 0.01 Monoterpenic ether
Linalool 5.43 Monoterpenic alcohol
1,3,8-para-Menthatriene 0.01 Monoterpene
endo-Fenchol 0.04 Monoterpenic alcohol
trans-Pinene hydrate 0.01 Monoterpenic alcohol
trans-para-Mentha-2,8-dien-1-ol 0.02 Monoterpenic alcohol
α-Campholenal 0.01 Monoterpenic aldehyde
allo-Ocimene 0.01 Monoterpene
cis-Limonene oxide 0.03 Monoterpenic ether
trans-Pinocarveol 0.11 Monoterpenic alcohol
trans-Limonene oxide 0.02 Monoterpenic ether
Dihydrolinalool 0.06 Synthetic
Camphor 0.14 Monoterpenic ketone
(E)-Myroxide 0.04 Monoterpenic ether
trans-Verbenol 0.04 Monoterpenic alcohol
Menthone 0.01 Monoterpenic ketone
Isoborneol 0.51 Monoterpenic alcohol
Pinocarvone 0.03 Monoterpenic ketone
Phellandrenol analog I 0.02 Monoterpenic alcohol
Borneol 0.96 Monoterpenic alcohol
(E)-2,6-Dimethyl-1,5,7-octatrien-3-ol 0.03 Monoterpenic alcohol
Terpinen-4-ol 0.11 Monoterpenic alcohol
para-Cymen-8-ol 0.06 Monoterpenic alcohol
α-Terpineol 1.65 Monoterpenic alcohol
Myrtenal 0.03 Monoterpenic aldehyde
Myrtenol 0.07 Monoterpenic alcohol
Methylchavicol 0.16 Phenylpropanoid
trans-Carveol 0.04 Monoterpenic alcohol
Nerol 0.05 Monoterpenic alcohol
cis-Carveol 0.03 Monoterpenic alcohol
Citronellol 0.11 Monoterpenic alcohol
Unknown 0.02 Oxygenated monoterpene
Neral 0.59 Monoterpenic aldehyde
Carvone 0.02 Monoterpenic ketone
Geraniol 0.84 Monoterpenic alcohol
Chavicol 0.16 Phenylpropanoid
Geranial 0.87 Monoterpenic aldehyde
Unknown 0.04 Oxygenated monoterpene
Bornyl acetate 0.07 Monoterpenic ester
Geranyl formate 0.02 Monoterpenic ester
Limonene cis-glycol 0.01 Monoterpenic alcohol
α-Cubebene 0.06 Sesquiterpene
Eugenol 0.91 Phenylpropanoid
α-Copaene 0.19 Sesquiterpene
β-Bourbonene 0.02 Sesquiterpene
β-Cubebene 0.02 Sesquiterpene
β-Elemene 0.11 Sesquiterpene
Isocaryophyllene 0.03 Sesquiterpene
Methyleugenol 0.02 Phenylpropanoid
β-Caryophyllene 11.40 Sesquiterpene
Caryophylla-4(12),8(13)-diene 0.04 Sesquiterpene
trans-α-Bergamotene 0.34*Sesquiterpene
α-Guaiene [0.34]*Sesquiterpene
α-Humulene 2.62 Sesquiterpene
allo-Aromadendrene 0.03 Sesquiterpene
cis-Muurola-4(15),5-diene 0.06 Sesquiterpene
trans-Cadina-1(6),4-diene 0.02 Sesquiterpene
γ-Muurolene 0.02 Sesquiterpene
Germacrene D 0.15 Sesquiterpene
β-Selinene 0.03 Sesquiterpene
α-Selinene 0.03 Sesquiterpene
β-Alaskene 0.02 Sesquiterpene
α-Muurolene 0.01 Sesquiterpene
δ-Guaiene 0.06 Sesquiterpene
γ-Cadinene 0.17 Sesquiterpene
trans-Calamenene 0.06 Sesquiterpene
δ-Cadinene 0.09 Sesquiterpene
Selina-4(15),7(11)-diene 0.08 Sesquiterpene
Selina-3,7(11)-diene 0.13 Sesquiterpene
(E)-α-Bisabolene 0.06 Sesquiterpene
α-Elemol 0.08 Sesquiterpenic alcohol
Isocaryophyllene epoxide B 0.02 Sesquiterpenic ether
Epiglobulol 0.16 Sesquiterpenic alcohol
(E)-Nerolidol 10.76 Sesquiterpenic alcohol
Caryophyllene oxide 0.90 Sesquiterpenic ether
Caryophyllene oxide isomer 0.10 Sesquiterpenic ether
Unknown 0.18 Unknown
Globulol 0.06 Sesquiterpenic alcohol
Viridiflorol 0.08 Sesquiterpenic alcohol
Guaiol 0.24 Sesquiterpenic alcohol
Humulene epoxide II 0.09 Sesquiterpenic ether
10-epi-Cubenol 0.06 Sesquiterpenic alcohol
α-Corocalene 0.05 Sesquiterpene
Caryophylladienol II 0.02 Sesquiterpenic alcohol
τ-Cadinol 0.14 Sesquiterpenic alcohol
α-Bisabolol 0.04 Sesquiterpenic alcohol
5-Ethenyl-1,5-bis(4-methyl-3-penten-1-yl)-cyclohexene? 0.03 Diterpene
4-Ethenyl-1,4-bis(4-methyl-3-penten-1-yl)-cyclohexene? 0.02 Diterpene
meta-Camphorene 0.26 Diterpene
para-Camphorene 0.10 Diterpene
Stearic acid 0.16 Aliphatic acid
Δ9-Tetrahydrocannabinol (Δ9-THC) 1.39 Terpenophenolic
Cannabinol (CBN) 0.13 Terpenophenolic This extraction resulted in a Consolidated total approx. 98% weight counted, 129 ingredients plus THC & Cannabinol.

The disclosed method, when practiced, yields unexpected and surprising results. Specifically, it resulted in:
129 terpenes and isolates identified, not just the 13 conventional ingredients mentioned in the literature.
First three fractions (Fractions B, C and D) are medicinal scented due to high level of Camphene, low Humulene, low Nerolidol.

Fourth fraction (Fraction F) has a fresh scent due to increased Myrcene, Delta 3 Carene, beta Phellandrene, and high level of limonene at 22.63%.

Fifth fraction (Fraction F) has a floral freshness due to high limonene 25.15% plus geranial, neral (ctiral), geraniol, alpha terpineol, Borneol, and isoBorneol.

Sixth fraction (Faction G) has a woody floral scent due to highest level of Fenchone, plus geranial, geraniol, alpha terpineol, Borneol, isoBorneol.

Rectified fraction (not distilled out) has a fresh woody floral aroma with a fruity undertone aromatic note. It has zero mono terpene, but higher sesquiterpenes (acyclic ring terpenes) alcohols, and oxygenated isolates.

With High Selectivity Fractional Distillation, we can modify the ratios of oxygenated ingredients, monoterpenes, sesquiterpenes and all isolates.

All distilled fractions have zero THC and CBD.

The Rectified fraction has all the THC and CBD.

The Rectified fraction has all the oxygenated material, none of the monoterpenes and all the sesquiterpenes.

We can control at will the ratio of the oxygenated, monoterpenes, sesquiterpenes and cannabinoids with High Selectivity Fractional Distillation. For example:

(10% vs 41%) Fraction C has the least amount of oxygenated ingredients (10%)

(81% vs 49%) Fractions B thru F have the maximum amount of monoterpene ingredients (B has 81% and F has 60%)

(1.5% vs 17%) Fractions C and D have the least amount of sesquiterpene ingredients.

Basically, we are unexpectedly capable of producing any fractions that are totally void of THC, CBD and monoterpenes.

We unexpectedly can reduce the oxygenated ingredients significantly to less than 10% from its normal high of 41%

We can unexpectedly almost eliminate the sesquiterpene content in our fractions to a low of 1.4% vs a normal high of 17% in the 5 extracts.

Using the disclosed method, we can minimize or maximize most components in the original blend. For example:

Nerolidol (at 11.2% in original blend) can be virtually eliminated in Fraction C, D and E (0.41%). That is a 96.5% elimination.

α-pinene (7.35%) can be reduced to 0.1% in the Rectified or 98.6% elimination and to 0.58% in G or 92.1% reduction.

Myrcene (11.11%) can be reduced to 0.14% in Rectified or 99.3% elimination and to 3.37% in G or 70% reduction.

β-pinene (6.925) can be reduced to 0.1% in Rectified or 99.9% elimination and to 2.84% in G or 60% reduction.

Linalool can be increased from 5.58% to 18.78% in Fr G or 237% increase and can also be decreased to 2.99% in Fr B or 46.5% decrease.

β-Caryophyllene can be increased from 11.86% to 26.76% or 126% increase and can also be decreased to 1.04% in Fr C or 91.2% decrease.

Caryophyllene oxide can be increased from 0.98% to 2.4% in Rectified or 145% increase and can almost be eliminated to 0.04% in Fraction C, D and E (a 96% decrease).

Δ-9-THC can be totally eliminated from 1.49% to zero in Fr C, D, E, F and G and can be increased to 3.25% in Rectified, a 118% increase (more than double).

CBN can be totally eliminated in Fractions B, C, D, E, F and G.

D-limonene (11.26%) can be totally eliminated in the Residue.

Neral/Geranial (Citral) can be virtually reduced to 0.24% from 1.47% or 84% reduction and can also be increased to 2.37% or 61% increase.

ɣ-Terpinolene can be reduced from 3.54% to 0.37%, a 90% reduction and can be increased to 11.16 in Fr G or 215% increase!

This discovery means that we can mimic various *cannabis*'s strains scent and flavor with this High Selectivity Fractional Distillation process with any one strain/one species of biomass.

More importantly we can enhance or reduce the pharmaceutical benefits of terpenes like enhancement of anti-anxiety and reduction of invigoration for better sleep.

Having the full control of modifying any fraction of components via our High Selectivity Fractional Distillation procedure will enhance the therapeutic benefits of the marijuana extracts. With reference to FIG. 4, the table illustrates the power of this process. See for example Fraction C which is almost void of alcohols (6.86%) and Sesquiterpenes (1.48%) but is predominantly made up of Monoterpenes (90.67%). Alternatively the Rectified fraction exhibits the opposite profile, namely, the Monoterpenes are almost eliminated (1.31%) while the Sequiterpene content ((39.81%) and the Alcohols ((43.07%) predominate.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments disclosed.

Insofar as the description above discloses any additional subject matter that is not within the scope of the claims below, the inventions are not dedicated to the public and the right to file one or more applications to claim such additional inventions is reserved.

What is claimed is:

1. A method for extracting and isolating aromatic compounds from *Cannabis* plant material comprising the steps of:

grinding the *cannabis* plant material to obtain a ground *cannabis*;

performing a $CO_2$ supercritical extraction upon a first portion of the ground *cannabis*, wherein said supercritical extraction is performed at a temperature below freezing, between −30 to 0 centigrade, for a period of 3 to 5 hours, at a pressure of between 1000-1300 psi;

performing a steam distillation on a second portion of the ground *cannabis*;

performing a butane extraction on a third portion of the ground *cannabis*, wherein the butane extraction is performed at a temperature between −30 to 0 centigrade;

performing an alcohol extraction on a fourth portion of the ground *cannabis*, wherein the alcohol extraction is performed at a temperature between −30 to 0 centigrade;

performing a maceration on a fifth portion of the ground *cannabis*, wherein the maceration is performed with coconut oil at a temperature of between 40-70 centigrade;

combining at least a portion of each resultant extracts from the CO2 supercritical extraction step, the steam distillation step, the butane extraction step, the alcohol extraction step and the maceration step to create a combined extract; and fractionally distilling the combined extract to separate aromatic compounds from the combined extract, wherein the fractional distillation step has at least six fractional temperature ranges, resulting in at least six different fractions.

2. The method of claim 1 wherein the steam distillation step is performed until substantially all THC and CBD present in the combined extract resides only in a rectified fraction.

3. The method of claim 1 wherein the at least six different fractions comprise differently scented aromatic flavors comprising:
   a) Medicinal A, Fraction B
   b) Medicinal B, Fraction C
   c) Medicinal C, Fraction D
   d) Citrus Fresh & Clean, Fraction E
   e) Floral, Fraction F
   f) Woodsy Floral, Fraction G and
   g) Sweet woodsy floral, Rectified fraction.

4. The method of claim 1 wherein the grinding step results in *cannabis* plant material that is ground to 7 mm or less particle size.

5. The method of claim 1 further comprising the step of pretreating the *cannabis* plant material with 1% w/w of 1 N Sodium hydroxide solution.

6. The method of claim 1 wherein the aromatic compounds comprise one or more of alpha-Bisabolol, Camphene, 3-Carene, beta-Caryophyllene, Citronellol, Cymene, Eucalyptol, Farnesene, Fenchol, Geraniol, Guaiol, Humulene, Isopropyltoluene, Isopulegol, Linalool, delta-Limonene, beta-Myrcene, Nerolidol, alpha-Pinene, Ocimene, alpha-Terpinene, gamma-Terpinene, and Terpinolene.

* * * * *